US00PP16195P2

(12) United States Plant Patent
Hooijman

(10) Patent No.: US PP16,195 P2
(45) Date of Patent: Jan. 10, 2006

(54) *ASTER* PLANT NAMED 'ESMORE'

(50) Latin Name: *Aster hybrida*
Varietal Denomination: Esmore

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 80 days.

(21) Appl. No.: 10/919,002

(22) Filed: Aug. 16, 2004

(51) Int. Cl.
*A01H 5/00* (2006.01)

(52) U.S. Cl. ..... Plt./355
(58) Field of Classification Search ..... Plt./355
See application file for complete search history.

*Primary Examiner*—Kent Bell
(74) *Attorney, Agent, or Firm*—C. A. Whealy

(57) ABSTRACT

A new and distinct cultivar of cut flower *Aster* plant named 'Esmore', characterized by its strong and erect flowering stems; symmetrical branching habit with long lateral branches; medium green-colored foliage; early, uniform and freely flowering habit; daisy-type inflorescences with white-colored ray florets; and excellent postproduction longevity.

2 Drawing Sheets

Botanical classification/cultivar designation: *Aster hybrida* cultivar Esmore.

BACKGROUND OF THE INVENTION

The present Invention relates to a new and distinct cultivar of cut flower *Aster* plant, botanically known as *Aster hybrida* and hereinafter referred to by the name 'Esmore'.

The new *Aster* is a product of a planned breeding program conducted by the Inventor in El Quinche, Pichincha, Ecuador. The objective of the breeding program is to create new cut flower *Aster* cultivars with durable leaves, strong stems, desirable floret colors and good postproduction longevity.

The new *Aster* originated from a cross-pollination made by the Inventor in El Quinche, Pichincha, Ecuador in February, 2000, of a proprietary *Aster* selection identified as Line 36, not patented, as the female, or seed, parent with an unknown *Aster* selection, not patented, as the male, or pollen, parent. The new *Aster* was discovered and selected by the Inventor as a single flowering plant within the progeny of the stated cross-pollination grown in a controlled environment in El Quinche, Pichincha, Ecuador. The selection of this plant was based on its durable foliage, strong stems and desirable inflorescence form and attractive ray floret color.

Asexual reproduction of the new *Aster* by vegetative tip cuttings was first conducted in El Quinche, Pichincha, Ecuador in January, 2001. Asexual reproduction by cuttings has shown that the unique features of this new *Aster* are stable and reproduced true to type in successive generations.

SUMMARY OF THE INVENTION

The cultivar Esmore has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Esmore'. These characteristics in combination distinguish 'Esmore' as a new and distinct cut flower *Aster:*

1. Strong and erect flowering stems.
2. Symmetrical branching habit with long lateral branches.
3. Medium green-colored foliage.
4. Early, uniform and freely flowering habit.
5. Daisy-type inflorescences with white-colored ray florets.
6. Excellent postproduction longevity.

Plants of the new *Aster* can be compared to plants of the female parent selection. Plants of the new *Aster* differ from plants of the female parent selection primarily in plant height as plants of the new *Aster* are taller than plants of the female parent selection. In addition, plants of the new *Aster* have more ray florets per inflorescence than plants of the female parent selection.

Plants of the new *Aster* can be compared to plants of the cultivar Sun Carlo, not patented. In side-by-side comparisons conducted in El Quinche, Pichincha, Ecuador plants of the new *Aster* differed from plants of the cultivar Sun Carlo in the following characteristics:

1. Plants of the new *Aster* were taller than plants of the cultivar Sun Carlo.
2. Plants of the new *Aster* had larger leaves than plants of the cultivar Sun Carlo.
3. Plants of the new *Aster* flowered about one week earlier than plants of the cultivar Sun Carlo.
4. Inflorescences of plants of the new *Aster* had more ray and disc florets than inflorescences of plants of the cultivar Sun Carlo.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster.*

The photograph on the first sheet comprises a side perspective view of a typical flowering plant of 'Esmore'.

The photograph on the second sheet are close-up views of a typical inflorescence of 'Esmore' (left) and a typical inflorescence of 'Sun Carlo' (left).

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown and flowered during the fall and winter in El Quinche, Pichincha, Ecuador, in an outdoor nursery and under conditions which approximate those generally used in commercial cut flower *Aster* production. During the production of these plants, day temperatures ranged from 12 to 30° C. and night temperatures ranged from 5 to 12° C. Plants were about four to six months from planting rooted young plants when the photographs and the botanical description were taken.

Botanical classification: *Aster hybrida* cultivar Esmore.

Parentage:

*Female, or seed, parent.*—Proprietary *Aster hybrida* selection identified as Line 36, not patented.

*Male, or pollen, parent.*—Unknown *Aster hybrida* selection, not patented.

Propagation:

*Type.*—Terminal vegatative cuttings.

*Time to initiate roots.*—About 12 to 16 days at 17 to 25° C.

*Time to produce a rooted young plant.*—About 21 to 25 days at 17 to 25° C.

*Root description.*—Fine, fibrous; 162D to 161D in color.

*Rooting habit.*—Freely branching.

Plant description:

*Appearance.*—Herbaceous daisy-type cut flower *Aster*. Flowering stems upright and strong. Vigorous. Symmetrical branching habit with long lateral branches.

*Plant height.*—About 111 cm.

*Plant width.*—About 28 cm.

*Lateral branches.*—Quantity per plant: About 27. Length: About 66 cm. Diameter: About 3.2 mm. Internode length: About 2.1 cm. Strength: Strong. Texture: Smooth, initially glabrescent, becoming glabrous with development; waxy. Color: 144B.

*Foliage description.*—Arrangement: Alternate, simple; sessile. Length: About 11.9 cm. Width: About 9 mm. Shape: Linear. Apex: Acute. Base: Cordate. Margin: Finely serrate. Texture, upper and lower surfaces: Glabrous, smooth; waxy. Color: Developing foliage, upper surface: 137B to 146A. Developing foliage, lower surface: 137A. Fully expanded foliage, upper surface: 137B; venation, 146C. Fully expanded foliage, lower surface: 146A to 137C; venation, 152A.

Inflorescence description:

*Appearance.*—Daisy-type inflorescence form with narrowly elliptic-shaped ray florets. Inflorescences terminal or axillary. Disc and ray florets develop acropetally on a capitulum. Inflorescences not fragrant. Inflorescences persistent. Inflorescences face mostly upright. Uniform and freely flowering habit.

*Flowering response.*—Plants flower year-round in Ecuador. Plants begin flowering about 13 weeks after planting.

*Postproduction longevity.*—Inflorescences maintain good color and substance for about two weeks as a cut flower and about 25 days on the plant.

*Quantity of inflorescences.*—About 18 inflorescences develop per lateral branch.

*Inflorescence bud.*—Height: About 6 mm. Diameter: About 5 mm. Shape: Nearly globose. Color: 137B to 143B.

*Inflorescence size.*—Diameter: About 2.7 cm. Depth (height): About 1.1 cm. Diameter of disc: About 1.1 cm. Receptacle height: About 6 mm. Receptacle diameter: About 9 mm.

*Ray florets.*—Number of ray florets per inflorescence/arrangement: About 38 in arranged in about two whorls. Length: About 1.3 cm. Width: About 3 mm. Shape: Narrowly elliptic. Apex: Acute to obtuse with emarginations. Base: Attenuate. Margin: Entire. Texture, upper and lower surfaces: Smooth, glabrous. Orientation: Initially upright, then mostly horizontal. Aspect: Mostly straight. Color: When opening, upper and lower surfaces: Close to 155D. Fully opened, upper and lower surfaces: Close to 155D.

*Disc florets.*—Arrangement: Massed at center of receptacle. Number of disc florets per inflorescence: About 34. Length: About 9 mm. Diameter, apex: About 2.4 mm. Diameter, base: About 0.7 mm. Shape: Tubular, salverform, elongated. Apex: Five lobes; lobes acute. Color, immature: 153A to 151B. Color, mature: Apex: 153D. Mid-section and base: 145C.

*Phyllaries.*—Quantity per inflorescence: About 51. Length: About 5 mm. Width: About 1 mm. Shape: Narrowly deltoid. Apex: Acute. Base: Truncate. Texture, upper and lower surfaces: Smooth, glabrous. Color, upper and lower surfaces: 137C to N144D.

*Peduncles.*—Length, terminal peduncle: About 1 cm. Length, fourth peduncle: About 1.6 cm. Length, seventh peduncle: About 2.4 cm. Diameter: About 1 mm. Aspect: Erect to about 22° from vertical. Strength: Strong. Texture: Pubescent. Color: 137C to 146A.

*Reproductive organs.*—Androecium: Present on disc florets only. Quantity per disc floret: One. Anther shape: Linear. Anther length: About 1.1 mm. Anther color: 6A. Pollen amount: Scarce. Pollen color: 6A. Gynoecium: Present on both ray and disc florets. Quantity per floret: One. Pistil length: About 9 mm. Stigma shape: Bilobed; lobes linear. Stigma color: 1B to 154B. Style length: About 5.4 mm. Style color: 145D. Ovary color: 1D to 145D.

*Seed.*—Length: With pappus, about 5 mm; without pappus, about 3 mm. Diameter: About 1 mm. Color: 145D; dried, 199A.

Disease/pest resitance: Resistance to pathogens and pests common to *Asters* has not been observed on plants grown under commercial greenhouse conditions.

Temperature tolerance: Plants of the new *Aster* have been observed to tolerate temperatures from about 7 to 30° C.

It is claimed:

1. A new and distinct cultivar of cut flower *Aster* plant named 'Esmore', as illustrated and decribed.

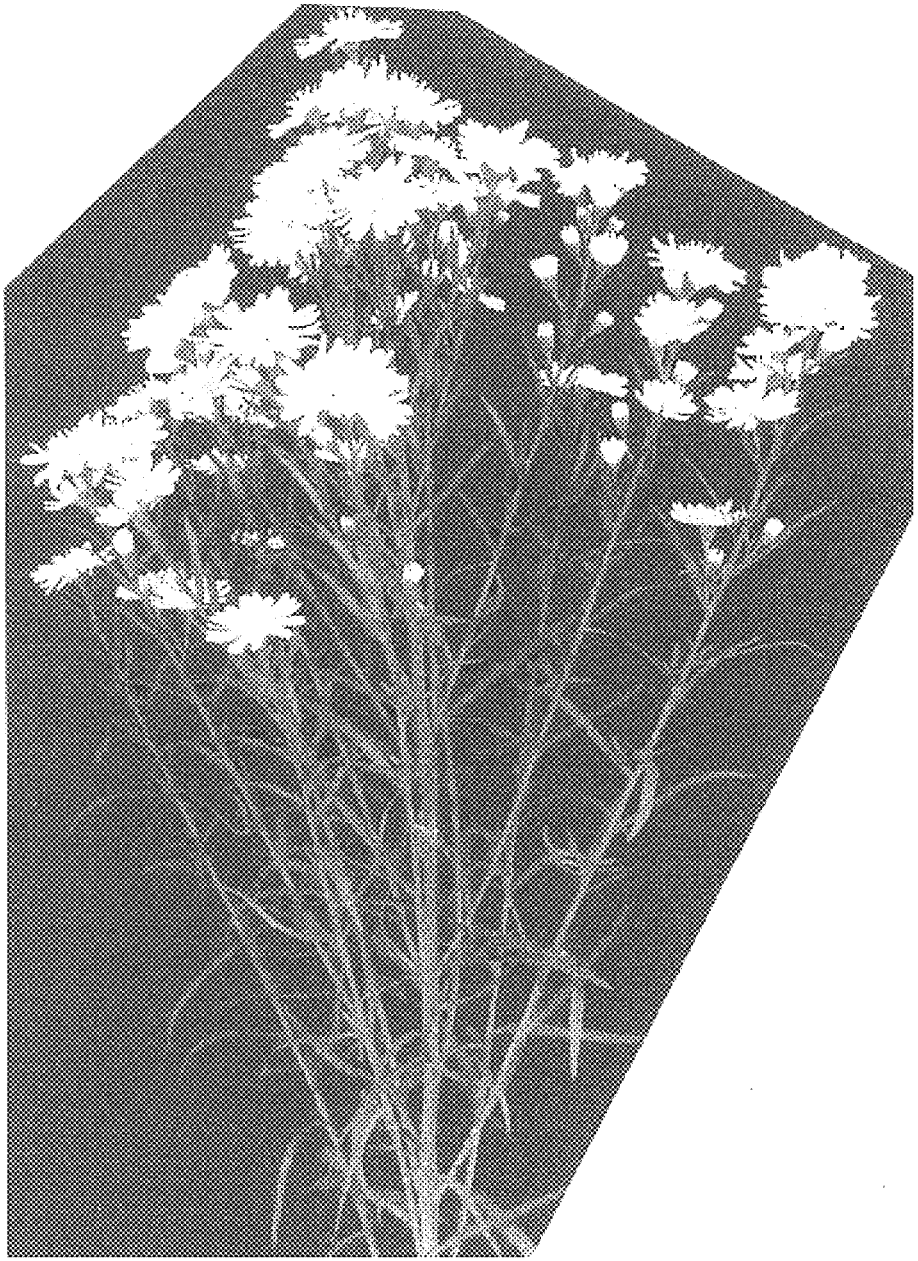

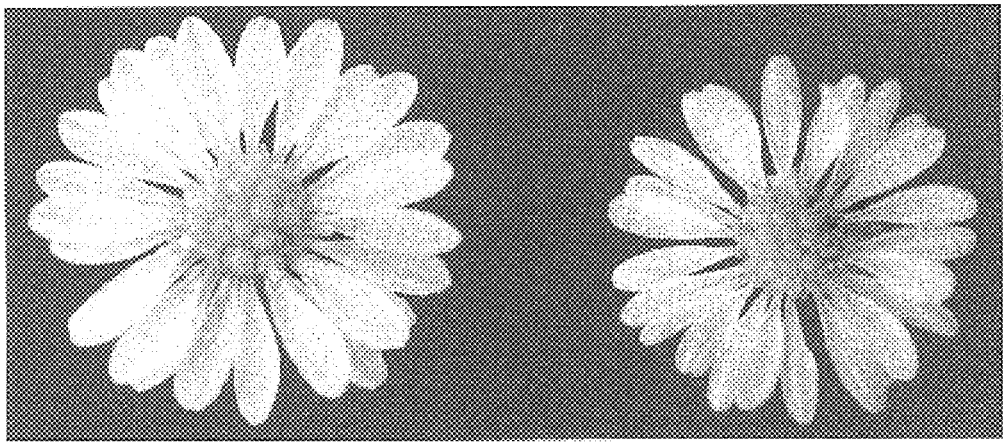

* * * * *